(12) United States Patent  (10) Patent No.: US 8,198,075 B2
Greenbaum et al.  (45) Date of Patent: *Jun. 12, 2012

(54) METHOD AND APPARATUS FOR ENHANCED DETECTION OF TOXIC AGENTS

(75) Inventors: Elias Greenbaum, Knoxville, TN (US); Miguel Rodriguez, Jr., Oak Ridge, TN (US); Jie Jayne Wu, Knoxville, TN (US); Hairong Qi, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 785 days.

This patent is subject to a terminal disclaimer.

(21) Appl. No.: 11/271,643

(22) Filed: Nov. 10, 2005

(65) Prior Publication Data

US 2008/0032326 A1  Feb. 7, 2008

Related U.S. Application Data

(63) Continuation-in-part of application No. 11/216,282, filed on Aug. 31, 2005.

(51) Int. Cl.
*C12M 1/00* (2006.01)
*C12M 1/34* (2006.01)
*C12M 1/36* (2006.01)
*C12M 1/38* (2006.01)
*C12M 3/00* (2006.01)
*C12N 1/00* (2006.01)

(52) U.S. Cl. ............ 435/292.1; 435/243; 435/283.1; 435/286.2; 435/287.1

(58) Field of Classification Search .................. None
See application file for complete search history.

(56) References Cited

U.S. PATENT DOCUMENTS

| | | | | |
|---|---|---|---|---|
| 3,790,461 A * | 2/1974 | Yeh | ................ | 204/553 |
| 4,267,038 A * | 5/1981 | Thompson | .................. | 210/602 |
| 4,909,919 A * | 3/1990 | Morris et al. | ................. | 204/603 |
| 5,313,264 A | 5/1994 | Ivarsson et al. | | |
| 5,426,306 A * | 6/1995 | Kolber et al. | .............. | 250/458.1 |
| 5,437,772 A * | 8/1995 | De Castro et al. | ............ | 205/775 |
| 5,602,446 A * | 2/1997 | Kolber et al. | .............. | 315/241 P |
| 5,670,031 A * | 9/1997 | Hintsche et al. | ........... | 205/777.5 |
| 5,779,911 A * | 7/1998 | Haug et al. | .................... | 210/739 |
| 5,817,954 A * | 10/1998 | Kahng et al. | ............... | 73/863.84 |
| 5,876,960 A * | 3/1999 | Rosen | ............................ | 435/39 |
| 6,051,437 A * | 4/2000 | Luo et al. | ...................... | 436/172 |
| 6,198,107 B1* | 3/2001 | Seville | ....................... | 250/458.1 |
| 6,486,588 B2 | 11/2002 | Doron et al. | | |
| 6,511,854 B1 | 1/2003 | Asanov et al. | | |
| 6,569,384 B2 | 5/2003 | Greenbaum et al. | | |
| 6,573,107 B1 | 6/2003 | Bowen et al. | | |
| 6,692,696 B1* | 2/2004 | Alberte | .......................... | 422/50 |
| 6,726,881 B2 | 4/2004 | Shinoki et al. | | |
| 6,783,647 B2* | 8/2004 | Culbertson et al. | .......... | 204/453 |
| 6,891,317 B2* | 5/2005 | Pei et al. | ........................ | 310/328 |
| 6,942,765 B2* | 9/2005 | Griego et al. | ................ | 204/199 |
| 6,964,857 B2* | 11/2005 | Greenbaum et al. | ............ | 435/29 |
| 7,015,484 B2* | 3/2006 | Gillispie et al. | ........... | 250/458.1 |
| 7,081,189 B2* | 7/2006 | Squires et al. | ................ | 204/451 |
| 7,214,427 B2* | 5/2007 | Huang et al. | .................. | 428/402 |
| 2006/0219939 A1 | 10/2006 | Satyanarayana et al. | | |

OTHER PUBLICATIONS

Collection of Abstracts . . . , University of Toyohashi , et al., 60 pp., 2002.*
Wu, J. et al. "Particle detection by electrical impedance spectroscopy with asymmetric-polarization AC electroosmotic trapping", 2005, Microfluid Nanofluid, 1:161-167.
Wu, J. et al. "Long-range AC electroosmotic trapping and detection of bioparticles", 2005, Ind. Eng. Chem. Res., 44:2815-2822.
Bhatt, K. et al. "An AC electrokinietic technique for collection and concentration of particles and cells on patterned electrodes", 2005, Langmuir, 21:6603-6612.

* cited by examiner

*Primary Examiner* — Debbie K Ware
(74) *Attorney, Agent, or Firm* — Brinks Hofer Gilson & Lione

(57) ABSTRACT

A water quality analyzer for real-time detection according to the invention comprises a biased AC electro-osmosis (ACEO) cell for receiving a fluid to be analyzed having a plurality photosynthetic organisms therein, and concentrating the plurality photosynthetic organisms into at least one concentrated region. A photodetector is provided for obtaining a measured photosynthetic activity of the plurality of photosynthetic organisms in the concentrated region, wherein chemical, biological or radiological agents reduce a nominal photosynthetic activity of the photosynthetic organisms. An electronics package analyzes the measured photosynthetic activity to indicate a presence of the chemical, biological or radiological agents in the fluid.

16 Claims, 4 Drawing Sheets

METHOD AND APPARATUS FOR ENHANCED DETECTION OF TOXIC AGENTS

CROSS REFERENCE TO RELATED APPLICATIONS

This application is a continuation-in-part (CIP) of application Ser. No. 11/216,282 entitled "Biosensor method and system based on feature extraction" which was filed on Aug. 31, 2005.

STATEMENT REGARDING FEDERALLY SPONSORED RESEARCH OR DEVELOPMENT

The United States Government has rights in this invention pursuant to contract no. DEAC05-00OR22725 between the United States Department of Energy and UT-Battelle, LLC.

FIELD OF THE INVENTION

The present invention relates to biosensors for detecting chemical, biological and/or radiological contaminants, or their precursors, in water or air.

BACKGROUND OF THE INVENTION

There is an increased awareness of the possibility of attacks on metropolitan areas using chemical, biological and radiological warfare agents. Researchers at the Oak Ridge National Laboratory (ORNL) have developed a biosensor system to detect toxic agents in primary-source drinking water, such as disclosed in U.S. Pat. No. 6,569,384 to Greenbaum et al. through the analysis of fluorescence induction curves. U.S. Pat. No. 6,569,384 to Greenbaum et al. discloses a water quality sensor for detecting the presence of at least one chemical or biological warfare agent. The sensor includes a cell, apparatus for introducing water into the cell and discharging water from the cell adapted for analyzing photosynthetic activity of naturally-occurring, free-living, indigenous photosynthetic organisms in water; a fluorometer for measuring photosynthetic activity of naturally-occurring, free-living, indigenous photosynthetic organisms drawn into the cell. An electronics package analyzes raw data from the fluorometer and emits a signal indicating the presence of at least one chemical or biological warfare agent in the water. Although the water quality sensor disclosed in U.S. Pat. No. 6,569,384 to Greenbaum et al. provides highly useful devices, it would be desirable to improve the speed and sensitivity of the device.

SUMMARY

A method of biosensor-based detection of toxins comprises the steps of concentrating a plurality photosynthetic organisms in a fluid to be analyzed into a concentrated region using biased AC electro-osmosis, and obtaining a measured photosynthetic activity of the photosynthetic organisms in the concentrated region, wherein chemical, biological or radiological agents reduce a nominal photosynthetic activity of the photosynthetic organisms. The presence of at least one of the agents, or precursors thereof, in the fluid is determined based on the measured photosynthetic activity. The plurality of photosynthetic organisms can be naturally-occurring, free-living, indigenous organisms in the fluid, such as native algae in water. The DC bias for the biased ACEO is generally from 1 to 10 volts.

Biased ACEO according to the invention provides significant fluorescent signal enhancement due to resulting enhanced concentration of the photosynthetic organisms. Enhanced concentration of the photosynthetic organisms significantly improving the sensitivity and speed of devices and methods according to the invention as compared to previous related devices and methods.

The photosynthetic activity can comprise chlorophyll fluorescence induction. A lab-on-a-chip system can be used for the concentrating step. The fluid can be drawn from a source of primary-source drinking water. In this embodiment, the method can further comprise the step of refreshing a supply of photosynthetic organisms by drawing a fresh supply of drinking water and repeating the method.

In a preferred embodiment of the invention, advanced signal processing algorithms are used utilized to detect the existence of the toxic agents. In such an embodiment, the determining step can further comprises the steps of providing at least one time-dependent control signal generated by a biosensor in the fluid medium, obtaining a time-dependent biosensor signal from the biosensor in the fluid medium to be monitored or analyzed for the presence of one or more of the chemical, biological or radiological agents; processing the time-dependent biosensor signal to obtain a plurality of feature vectors using at least one of amplitude statistics and a time-frequency analysis, and determining the presence of at least one of the agents, or precursors thereof, from the feature vectors based on reference to the control signal. The time-frequency analysis can comprise wavelet coefficient analysis. In one embodiment, both amplitude statistics and time-frequency analysis can be used in the processing step.

The method can further comprising the step of identifying which agents are present in the fluid. A linear discriminant method can be used for the identifying step. The linear discriminant method can comprise support vector machine (SVM) classification.

A water quality analyzer comprises a biased AC electro-osmosis (ACEO) cell for receiving a fluid to be analyzed having a plurality photosynthetic organisms therein and concentrating the plurality photosynthetic organisms into at least one concentrated region. A photodetector obtains a measured photosynthetic activity of the plurality of photosynthetic organisms in the concentrated region, wherein chemical, biological or radiological agents reduce a nominal photosynthetic activity of the photosynthetic organisms. An electronics package analyzes the measured photosynthetic activity to indicate a presence of the chemical, biological or radiological agents in the fluid. The ACEO cell can comprise a lab-on-a-chip device. The lab-on-a-chip device can include at least one electronic device on the chip. A structure can also be provided for communicating the measured photosynthetic activity or the measured photosynthetic activity after analysis by the electronics package to one or more remote sites.

BRIEF DESCRIPTION OF THE DRAWINGS

A fuller understanding of the present invention and the features and benefits thereof will be obtained upon review of the following detailed description together with the accompanying drawings, in which.

DETAILED DESCRIPTION

As noted in the background, conventional aquatic biosensors monitor the quality of primary-source drinking water by analyzing the fluorescence signal signature from healthy algae during photosynthesis. Fluorescence emitted by healthy algae differs from that emitted by algae exposed to a toxic agent. Relatively simple algorithms based on PSII efficiency are generally used to characterize the signature of the fluorescence signal. However, a major problem encountered in toxic detection is that microalgae are present at a low concentration so that reliable detection is often not possible.

Sensitivity and selectivity are critical for real-time detection of toxins. For selectivity, a tissue based detection system is preferably utilized which uses naturally-occurring aquatic photosynthetic tissue as the sensing material (microalgae) for detection of antagonists in the water. For sensitivity, the microbial concentration scheme uses biased AC electro-osmosis (ACEO), which is newly discovered and presently at the forefront of electrokinetic microfluidic research. ACEO rapidly enriches local microalgal concentration by expediting their diffusion via microfluidic convection to certain areas, thus allowing their concentration. Concentrated biosensors improves the resulting signal level, analogous to the function of an amplifier in an electronic circuit. Fluorescence techniques are then preferably used to assess the metabolic health of the biosensors.

A water quality analyzer for real-time detection according to the invention comprises a biased AC electro-osmosis (ACEO) cell for receiving a fluid to be analyzed having a plurality photosynthetic organisms therein, and concentrating the plurality photosynthetic organisms into at least one concentrated region. A photodetector, such as luminometer or fluorometer, is provided for obtaining a measured photosynthetic activity of the plurality of photosynthetic organisms in the concentrated region, wherein chemical, biological or radiological agents reduce a nominal photosynthetic activity of the photosynthetic organisms. An electronics package analyzes the measured photosynthetic activity to indicate a presence of the chemical, biological or radiological agents in the fluid. Specific agents can also be identified. For example, using characteristic fluorescence induction curves for a given library of agents, specific agents can be identified. Assuming the agent is a certain minimum concentration, the concentration of the agent may also be determined.

Figure 1:
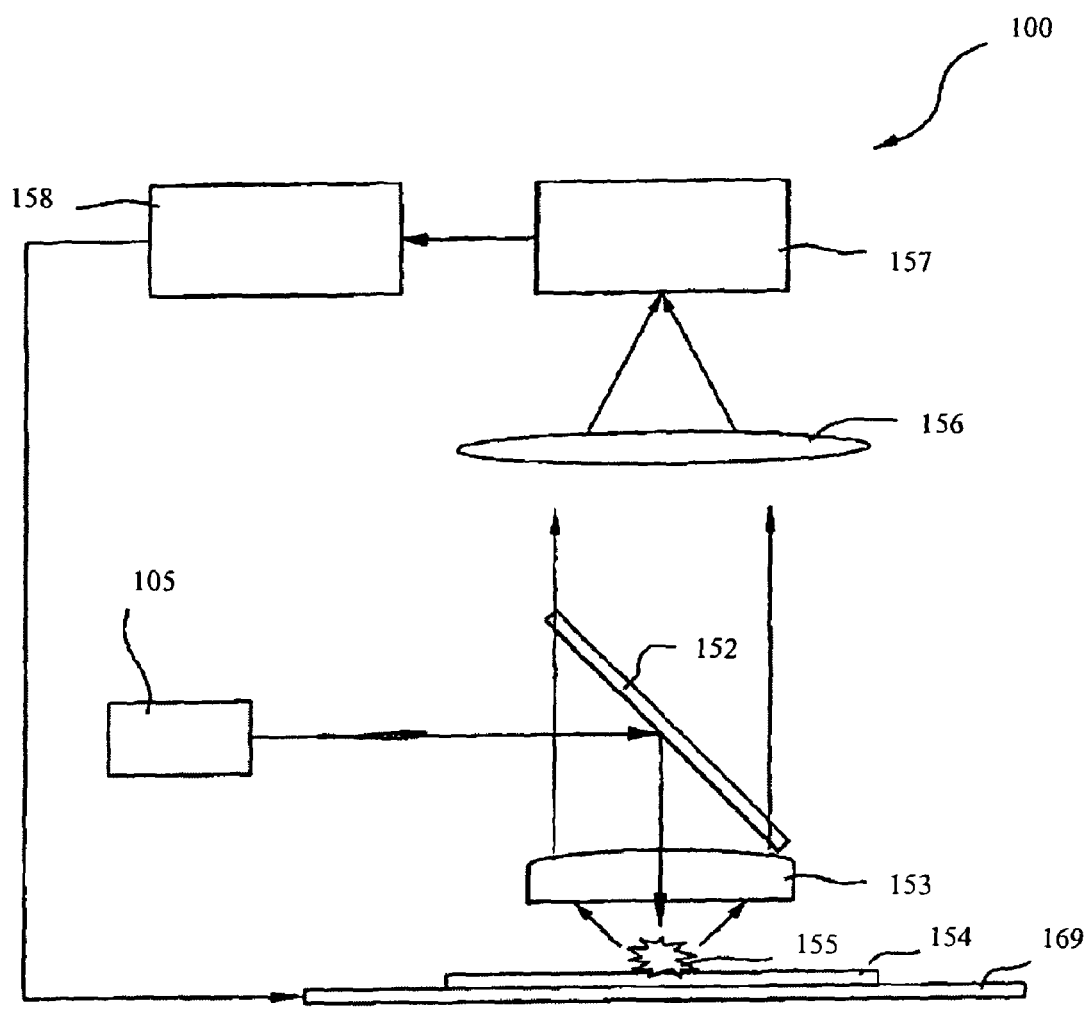
FIG. 1 is a schematic view showing an exemplary AC electro-osmosis (ACEO)-based water quality analyzing system 100, according to an embodiment of the present invention.

FIG. 1 is a schematic view showing an exemplary AC electro-osmosis (ACEO)-based water quality analyzing system 100, according to an embodiment of the present invention. The system 100 comprises a light source 105 for emitting light beam, a beam splitter 152 for redirecting the emitted light beam to a focusing lens 153. Focusing lens 153 focuses the light beam after reflection from beam splitter onto biased AC electro-osmosis (ACEO) trapping cell 154. When the photosynthetic organisms are bioluminescent, light source 105, beam splitter 152 and focusing lens 153 are not required. ACEO cell receives a fluid to be analyzed having a plurality photosynthetic organisms therein and concentrates the plurality photosynthetic organisms into at least one concentrated region therein. Light is directed towards the concentrated regions in ACEO cell 154 thus exciting the photosynthetic organisms on the ACEO cell 154 to produce fluorescence 155. A focusing lens 156 is provided for focusing the fluorescence on a photodetector 157 which detects the fluorescence. A computing device 158 receives the measured fluorescence signal detected by the photodetector 157.

The ACEO cell 154 is preferably disposed on a platform 169. The platform is generally movable under the control of computing device 158. Computing device is generally loaded with algorithms to analyze the fluorescence data as well as to control the movement of the platform 169.

There are generally two types of ACEO particle traps comprising the configurations of planar interdigitated electrodes and parallel plate electrodes. Planar interdigitated electrodes are generally preferred for the present invention. Parallel plates typically generate uniform electric field normal to the electrode surface. In this configuration, tangential electric fields are generated by asymmetric electrode patterns on the plates. Patterned electrodes are preferably provided as disclosed in a paper by Bhatt, et al (Bhatt, K. H., Grego, S., Velev, O. D. 2005; An AC electrokinetic technique for collection and concentration of particles and cells on patterned electrodes. *Langmuir,* 21(14):6603-6612). Electrodes face each other, in the form of parallel plates. The electric field is generated by Bhatt using a pure AC signal. No DC bias is disclosed or suggested by Bhatt. The non-uniform electric field gradients are realized through patterning one electrode with non-electrically conductive materials, such as photoresist, or silicon dioxide. Particles accumulate at the center of corrals where the flow velocity is relatively low.

In contrast to Bhatt, the invention preferably uses an AC signal together with a DC bias, referred to herein as "biased ACEO" to bias the electrodes. Biased ACEO takes advantage of different electrode polarizations which are not possible based on the AC only ACEO disclosed in Bhatt. Significantly, the inventive biased ACEO can produce a distinct line of particles, thus heavily concentrating the particles. For a plate separation of about 0.5 mm, the DC bias is generally in a range from 1 to 10 volts, while the AC signal has less than a 20 volt peak to peak amplitude and frequency of from 50 Hz to 1 MHz. Preferably, the voltage range is within 10 Vrms for DC and AC components combined.

Figure 2:
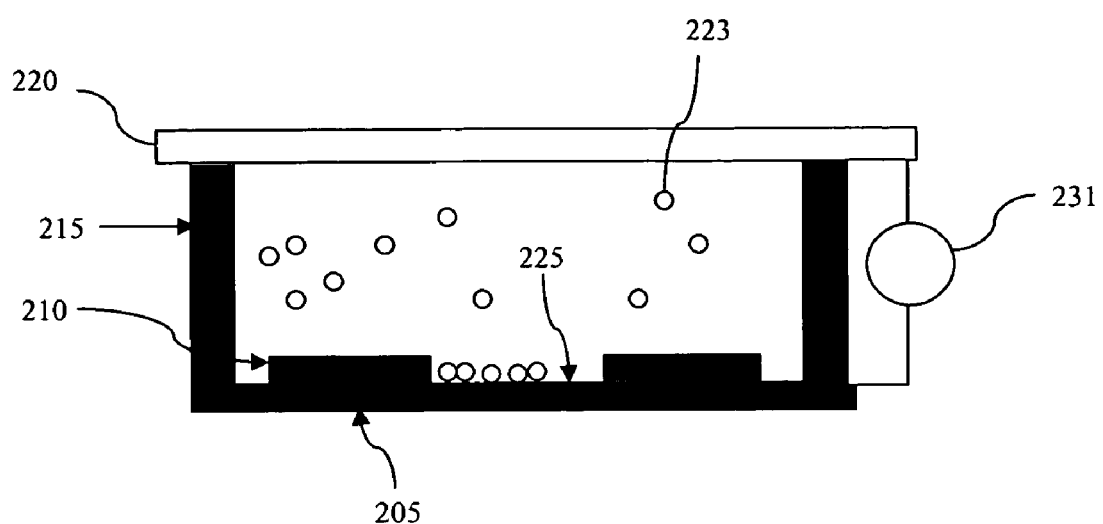
FIG. 2 shows an exemplary AC electro-osmosis (ACEO) cell based on planar interdigitated electrodes, according to an embodiment of the present invention.

An exemplary ACEO cell 200 based on planar interdigitated electrodes is shown in FIG. 2. A substrate support 205 having at least semiconducting electrical conductivity is provided to provide a bottom electrode, such as an n- or p-doped silicon wafer 205. A patterned layer of an electrically insulating material 210, such as silicon dioxide, is disposed on the substrate support 205. An electrically insulating spacing material 215 surrounds and seals the periphery of cell 200 to allow a liquid to be analyzed to be held within the cell. Any substrate 205 can generally be used, as long as an electrically conductive layer is placed on top of the substrate 205 and that electrically conductive layer is exposed to the fluid.

The exposed patterned electrode is generally realized either by applying another layer of insulting layer or by etching the conductive layer. Fluid stagnation forms at the center of the electrode patterns 225 where the photosynthetic organisms 223 get concentrated.

The nominal height of spacing material is generally on the order of hundreds of microns. An optically transparent top electrode 220 in the wavelength range of interest, such as an indium-tin-oxide coated glass layer, is disposed on spacing material to complete the cell enclosure. A plurality of photosynthetic organisms 223 are disposed inside cell 200. A power supply 231 which provides an AC signal riding on a DC bias applies an electrical signal across top electrode 220 and bottom electrode 205. Although not shown, separate power supplies for the AC signal and the DC bias can be used.

Figure 3:
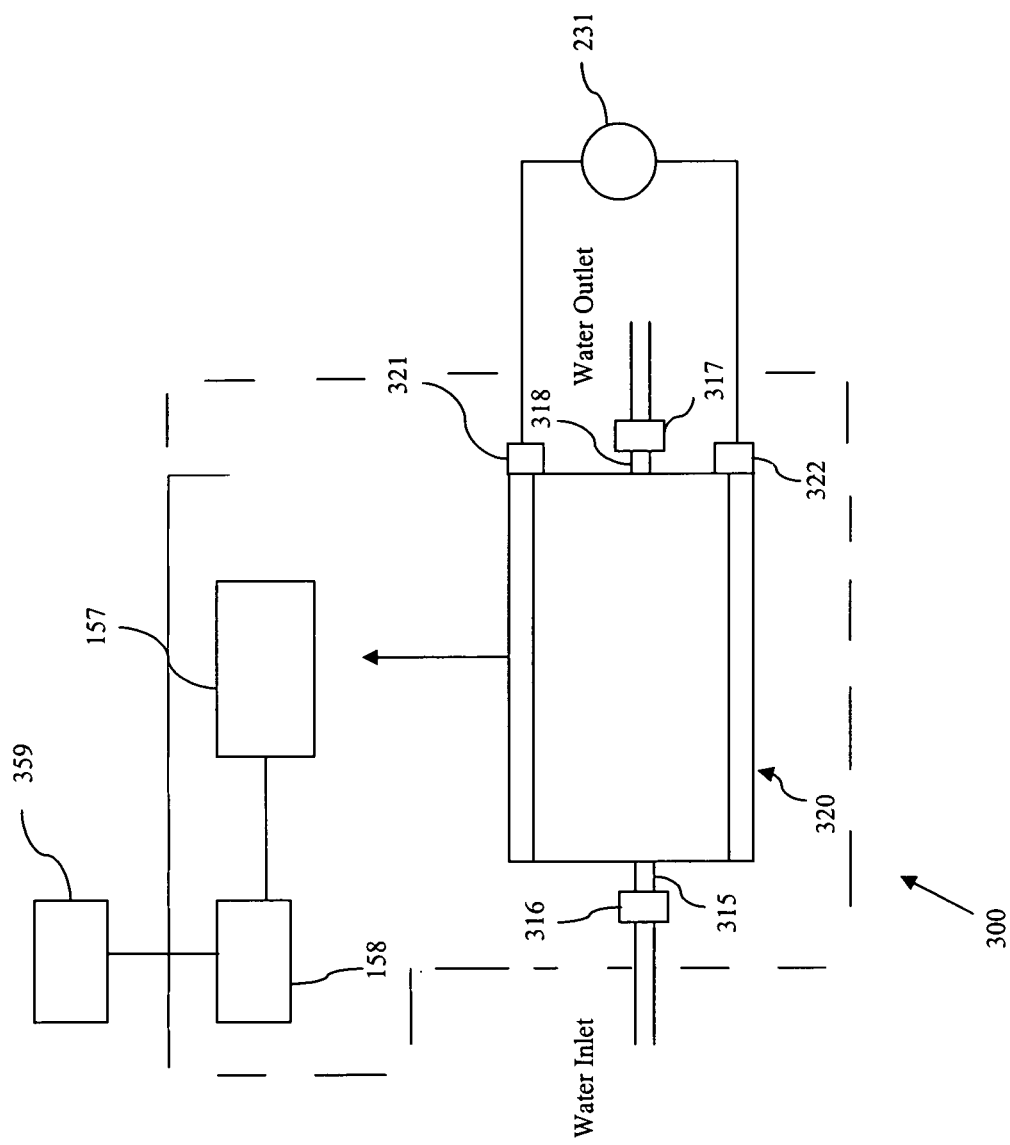
FIG. 3 shows a schematic of preferred embodiment of the ACEO cell-based system along with related interface devices, according to an embodiment of the present invention. The ACEO trapping cell is embodied as a lab-on-a-chip device in this preferred embodiment.

FIG. 3 shows a preferred embodiment of the ACEO cell-based system 300 along with related interface devices. ACEO trapping cell is embodied as a lab-on-a-chip device 320 in this preferred embodiment. The lab-on-a-chip provides rapid and sensitive biological and clinical analyses on a single, miniaturized device. Lab-on-a-chip devices are a subset of MEMS devices.

There are several advantages to the lab-on-a-chip embodiment along with microalgae sensors, including rapid detection time from electrokinetic enrichment, specificity as a result of using microalgae as sensors, and simplicity since the detection components are located on a single platform. The lab-on-a-chip technology also provides portability and reduced analysis time. The reduction of sample and reactant volume increases the efficiency and reduces the costs associated with analytical chemistry and analytical biochemistry. Additionally, microfabrication provides the possibility of mass production. As shown by the dashed line in FIG. 3 which indicates a single chip, lab-on-a-chip device 320, as well as electronic components such as photodetector 157 and computing device 158 can be fabricated on the same chip.

Electrical contact to lab-on-a-chip device 320 is provided by external electrodes 321 and 322. An AC power supply 231 provides the required bias to realize ACEO and forces the biosensors into at least one concentrated region. In one embodiment, a battery (not shown) provides the power for the various components of system 300.

Lab-on-a-chip device 320 includes a water inlet 315 and water outlet 318. Water is generally driven into inlet 315 by a small internal pump 316 that are commonly used for lab-on-a-chip devices. Water is also drawn out from outlet 318 by small internal pump 317. Periodically, new samples of water are preferably analyzed by system 100 using a "batch mode" rather than a "continuous mode". One unique aspect of the invention is that unlike conventional sensing devices, this sensor material is external to the detecting instrument and can be continuously refreshed. Such systems thus may be used as continuous rapid-warning sentinels for detection of chemical warfare agents in sunlight-exposed drinking water supplies.

System 100 includes a structure for communicating measured and/or analyzed data to one or more remote sites 359. The remote sites can be military or civilian sites. For example, in military applications, military personnel could use the invention in the field. In civilian applications, water utilities personnel may use the invention at the intake points for water reservoirs located far from their water treatment plant or distribution facility. For example structure for communicating 359 can comprise Wi-Fi™ card 150. Card 150 connects to a local area network (LAN) when near a network access point. The connection is made by radio frequency signals. If the local area network is connected to the Internet, the Wi-Fi device can have Internet access as well. Alternatively, structure for communicating 359 can comprise an RS 232 interface or equivalent for serial binary data interconnection of the measured data and or analyzed data.

In one embodiment, raw data received from the photodetector 157 is transmitted by Wi-Fi™ 359 through a LAN to a remote cite where a processor/computer is located (not shown). The processor/computer obtains the measured photosynthetic activity of the photosynthetic organisms in the concentrated region, and applies an algorithm to determining a presence of chemical, biological or radiological agents, or precursors thereof, based on the measured photosynthetic activity, and in a preferred embodiment can also determine the specific agent as well as its concentration.

In one embodiment of the invention, water samples can be stored and time stamped. In a preferred embodiment of the invention, an operator can detect at what time and date the samples were collected to permit further analysis to comply with regulatory mandates (e.g. federal, state, city, industrial, etc.) in the event of the detection of a severe toxic agent. Microchannels on the lab-on-a-chip 320 can be used for this purpose. In a preferred embodiment of the invention, the system allows the operator to remove designated chips/cartridges containing the microchannels storing the water collected from such an event. By activating certain internal pumps or opening certain water lines and deactivating other pumps or closing certain water lines, the system could be designed to direct the water from the main set of microchannels to the ones used for storing purposes.

Figure 4:
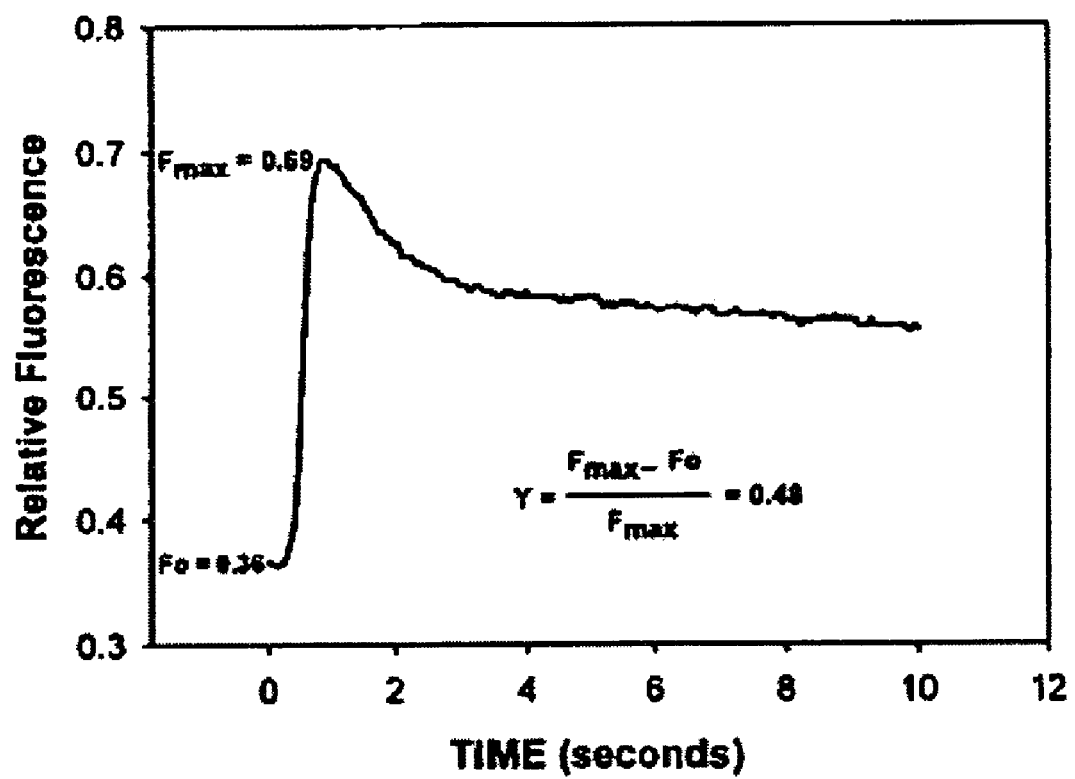
FIG. 4 is an exemplary fluorescence induction curve.

In order to detect the existence of toxic agents, the traditional method is to measure the so-called "efficiency of PSII (photosystem II) photochemistry";

$$PSII \text{ efficiency} = \frac{F_{max} - F_s}{F_{max}}$$

where $F_s$ is the value at the stable time and $F_{max}$ is the maximum value of the fluorescence induction curve, as shown in FIG. 4. The PSII efficiency represents a simple induction curve-based calculation of the fluorescence signal "signature", and significant deviations thereof indicate the potential presence of a toxic agent in the water.

Although PSII efficiency is generally effective in detecting the presence of toxic agents, it fails in some cases due to the non-significant photochemical yield presented by certain toxic agents. Moreover, it cannot generally classify between different agents or the same agent with different concentrations. In addition, using this parameter it can take as long as 60 minutes to arrive at a decision regarding detection of a contamination event. The classification of different agents with a shorter response time is of profound importance, such as to reduce response time to a contamination event. With the knowledge of the type of toxic agent, appropriate medicine and rescue strategies can be used in time to save lives as well as counter the terrorist attacks.

In a preferred embodiment, the advanced signal processing algorithms disclosed in parent application Ser. No. 11/216,282 are utilized to detect the existence of toxic agents. This advanced analysis methodology comprises the steps of providing at least one time-dependent control signal generated by a biosensor in a liquid (e.g. water) or a gas (e.g. air), and obtaining a time-dependent biosensor signal from the biosensor in a gas or liquid medium to be monitored or analyzed for the presence of one or more toxins selected from chemical, biological or radiological agents. The time-dependent biosensor signal is processed to obtain a plurality of feature vectors using at least one of amplitude statistics and a time-frequency analysis. At least one parameter relating to the toxicity of the gas or liquid medium is then determined from the feature vectors based on reference to the control signal provided. As used herein, the phrase "feature vector" is defined as (i) summation based statistical measures as described below (amplitude statistics) and (ii) coefficients (e.g. wavelet coefficients), or statistical parameters derived from the coefficients (e.g. wavelet coefficient standard deviation) generated by application of a time-frequency analysis to the time-dependent sensor signal.

A first new algorithm comprises high-order statistical analysis (referred to herein as "amplitude statistics") of the light signal in the time domain. As used herein, the phrase "amplitude statistics" is defined as summation based statistical measures derived from a plurality of (N) time points in the signal curve, such as first order (mean), second order (standard deviation), third order (skewness), and fourth order (kurtosis). PS II efficiency as described in U.S. Pat. No. 6,569,384 to Greenbaum et al. is thus clearly not amplitude statistics since the measurement therein is based on the simple difference between discrete points being the maximum value of the fluorescence induction curve ($F_{max}$) and the fluorescence value at the stable time ($F_s$).

Amplitude statistics can capture more dynamic features of the signal than PSII efficiency, including how fast the signal approaches maximum and minimum, how far samples are from the mean value, and how symmetric the signal appears. These features are generally required in the detection and identification regarding the existence of different toxic agents.

A first new algorithm comprises wavelet analysis of the light signal in the time-frequency domain referred to herein as "time-frequency analysis". Because of the nature of the light signal captured by the aquatic biosensors, time-frequency analysis can reveal when and how the frequency of the signal changes. In a preferred embodiment, only three features extracted from the wavelet coefficients are used in the algorithm instead of the entire set of coefficients for signal characterization.

Amplitude statistics and time-frequency analysis according to the invention can be used independently to provide detection results significantly improved as compared to algorithms based on the fluorescence signal signature. However, by combining amplitude statistics and time-frequency analysis, the confidence detection and identification can be improved to an even higher level.

The photosynthetic organisms are generally cell-based, and can include genetically modified cells. For example, a bacterium modified with lux genes can be used. In the case of fluorescence induction, algae can be used, either naturally-occurring or genetically modified. Naturally-occurring aquatic algae are generally preferred as they does not generally require culturing.

Every water source that is exposed to sunlight contains populations of photosynthetic microorganisms (phytoplankton and algae, for example), at concentrations ranging from 10 to as high as 100,000 organisms/ml. Although always present in sunlight-exposed water, these microorganisms are often invisible to the unaided eye. Phytoplankton emits a characteristic fluorescence signal that, if detectable in solutions with low microorganism concentrations, can be utilized as an in situ indicator of chemical and/or biological warfare agents in water supplies. Biosensors provide time-dependent biosensor signal while in a gas or liquid medium to be monitored or analyzed for the presence of one or more toxins selected from chemical, biological or radiological agents. Water-soluble toxic chemical and/or biological agents, for example, can include blood agents (cyanide, for example), pesticides (methyl parathion, for example) and herbicides (DCMU, for example), or radionuclide that could pose a threat to primary-source drinking water supplies.

The time-dependent biosensor signal is modified by the toxin as compared to a control signal when the toxin is absent. Although the invention is generally described in terms of spectroscopic signals (e.g. fluorescent), other signals can be utilized. Regarding acoustic signals, see, e.g., U.S. Pat. No. 6,486,588 to Doron, et al. "Acoustic biosensor for monitoring physiological conditions in a body implantation site"; "Acoustic immunosensor for real-time sensing of neurotransmitter GABA", *Proceedings of the 25$^{th}$ IEEE Annual International Conference,* 4:2998-3000.+Khraiche, M. L., Zhou, A., Muthuswamy, J. 2003, and "Acoustic sensors for monitoring neuronal adhesion in real-time", *Proceedings of the 25$^{th}$ IEEE Annual International Conference,* 3:2186-2188.). Regarding electrochemical signals, see, e.g., U.S. Pat. No. 6,511,854 to Asanov, et al. "Regenerable biosensor using total internal reflection fluorescence with electrochemical control", and "Development and evaluation of electrochemical glucose enzyme biosensors based on carbon film electrodes" *Talanta,* 65(2):306-312.+Xu, J.-Z., et al. 2004.

Regarding thermal detection, see e.g.,"Calorimetric biosensors with integrated microfluidic channels. *Biosensors and Bioelectronics",* 19(12):1733-1743.+Towe, B. C., Guilbeau, E. J. 1996. Regarding magnetic based sensors, see de Oliveira, J. F., et al. 2005 "Magnetic resonance as a technique to magnetic biosensors characterization in Neocapritermes opacus termites" *Journal of Magnetism and Magnetic Materials,* 292(2):e171-e174.+Chemla, Y. R., et al. 2000, "Ultrasensitive magnetic biosensor for homogeneous immunoassay", *Proc. Natl. Acad. Sci. USA,* 97(26):14268-72. Regarding surface plasmon resonance (SPR) using enzymes or antibodies see, e.g., U.S. Pat. No. 6,726,881 to Shinoki, et al. "Measurement chip for surface resonance biosensor", U.S. Pat. No. 6,573,107 to Bowen, et al. "Immunochemical detection of an explosive substance in the gas phase through surface plasmon resonance spectroscopy", U.S. Pat. No. 5,313,264 to Ivarsson, et al. "Optical biosensor system".

Toxic substances often appear in primary-source drinking waters because of unintentional industrial activity or potentially deliberate human action, and its real-time detection is of great importance because bioterrorism and environment contamination are on the rise around the globe. Current practices of prevention rely on real-time monitoring. Since the threat of toxins to societies could be substantially mitigated with early detection, the demand for rapid detection of low concentration toxins is expanding quickly for both civilian and military applications to improve homeland security. The invention can detect toxins at very low concentrations, particularly when embodied using the preferred lab-on-a chip cell, thus providing an earlier warning than previously possible. Systems according to the invention will provide a unique advantage to managers of water utility facilities at civilian and military installations for early detection in the event of a contamination event.

EXAMPLES

It should be understood that the Examples described below are provided for illustrative purposes only and do not in any way define the scope of the invention.

In a first experiment, high-efficiency bioparticle concentration was demonstrated using an ACEO cell with a DC bias of less than 3 volts. It was found that about 60 cells *Escherichia coli* were collected into a surface area of 10 μm×10 μm from a suspension of $10^6$ particles/ml (*E. coli* cells were about 100 μm apart in the solution) within 30 seconds.

In another experiment, *Chlorella vulgaris* (a green alga) was selected as the model bioparticle. To maximize detection signals, thin film metal electrodes with feature sizes of micrometer and nanometer, comparable to those of bioparticles, were used to study electrokinetic capture of bioparticles and their autofluorescence on these electrodes.

Measuring the impedance of detection electrodes at electrical signals suitable for bioparticle trapping, a resolution better than $10^4$ bacteria/ml and impedance differentiation between two types of bioparticles were obtained. Bioparticles attracted to the electrodes reduce the impedance measured between the pair of electrodes. So by comparing the measured impedance reading with a control sample, the difference in impedance will indicate the presence of the biparticles.

A video file was obtained with the alga *Chlorella vulgaris*. The results obtained demonstrated that electrofocusing can increase local concentration of microalgae by several orders of magnitude in real-time. In the video file, the cells formed a single file at the left electrode. Each electrode was about 70 micrometers (μm) in diameter.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A water quality analyzer, comprising:
a cell for receiving a fluid to be analyzed and concentrating a plurality of photosynthetic organisms in said fluid to be analyzed into at least one concentrated region within the cell, said cell comprising:
   a first electrode and a top electrode arranged opposite to one another, each having a surface in contact with said fluid flowing therebetween, wherein the top electrode is optically transparent to photosynthetic radiation produced by the plurality of photosynthetic organisms, wherein the first electrode and the top electrode are separated by first and second electrically insulating spacers, wherein the first electrode, first spacer, second spacer, and top electrode are arranged to form a conduit that the fluid flows through, and
   a power supply electrically connected to the first electrode and the top electrode, the power supply for producing an AC signal with a DC bias across the first electrode and the top electrode;
a photodetector for obtaining a measured photosynthetic activity of said plurality of photosynthetic organisms in said at least one concentrated region, wherein chemical, biological, or radiological agents reduce photosynthetic activity of said photosynthetic organisms;
an electronics package for analyzing measured photosynthetic activity to indicate a presence of said chemical, biological, or radiological agents in said fluid; and
a platform on which the cell is disposed, wherein the platform is moveable relative to the photodetector as controlled by the electronics package.

2. The water quality analyzer of claim 1, wherein said water quality analyzer comprises a lab-on-a-chip device that includes the cell.

3. The water quality analyzer of claim 2, wherein the photosynthetic activity comprises fluorescence induction using naturally occurring algae.

4. The water quality analyzer of claim 1, further comprising a structure for communicating said measured photosynthetic activity, said measured photosynthetic activity after analysis by said electronics package, or both, to one or more remote processors or computers.

5. The water quality analyzer of claim 1 further comprising an electrically insulating material disposed on the first electrode, wherein the electrically insulating material includes patterns, such that the at least one concentrated region comprises at least one of the patterns.

6. The water quality analyzer of claim 1, wherein said power supply produces a DC signal ranging from 1 to 10 volts, an AC signal less that 20 volt peak-to-peak amplitude, or both.

7. The water quality analyzer of claim 1, wherein the cell comprises planar interdigitated first and top electrodes.

8. A water quality analysis system comprising:
an electro osmosis cell for receiving a fluid to be analyzed and concentrating a plurality of photosynthetic organisms in the fluid to be analyzed within the cell, wherein the cell comprises:
   a bottom electrode and a top electrode arranged opposite to one another, the bottom electrode having a surface in contact with the fluid in the cell, wherein the top electrode is optically transparent to photosynthetic radiation produced by the plurality of photosynthetic organisms, further wherein the bottom electrode comprises an electrically insulating material that includes patterns such that the photosynthetic organisms in the fluid are concentrated in at least one of the patterns for analysis, and
   a power supply electrically connected to the bottom electrode and the top electrode, the power supply for producing an AC signal with a DC bias across the bottom electrode and the top electrode, where the electrodes have different polarizations;
a photodetector for obtaining a measured photosynthetic activity of the concentrated plurality of photosynthetic organisms, wherein chemical, biological, or radiological agents reduce photosynthetic activity of the photosynthetic organisms;
an electronics package for analyzing measured photosynthetic activity to indicate a presence of the chemical, biological, or radiological agents in the fluid; and
a platform on which the cell is disposed, wherein the platform is moveable relative to the photodetector and is controlled by the electronics package.

9. The water quality analysis system of claim 8, wherein said water quality analysis system comprises a lab-on-a-chip device that includes the cell.

10. The water quality analysis system of claim 8, wherein the photosynthetic activity comprises chlorophyll fluorescence induction.

11. The water quality analysis system of claim 8, further comprising a structure for communicating the measured photosynthetic activity, the measured photosynthetic activity after analysis by the electronics package, or both, to one or more remote processors or computers.

12. The water quality analysis system of claim 9, wherein the lab-on-a-chip device further comprises the photodetector, the electronics package, an external electrode, a water inlet, a water outlet, a pump, or a combination thereof.

13. The water quality analysis system of claim 8, wherein said power supply produces a DC signal ranging from 1 to 10 volts, an AC signal less than 20 volt peak-to-peak amplitude, or both.

14. The water quality analysis system of claim 8, wherein the cell comprises planar interdigitated bottom and top electrodes.

15. The water quality analysis system of claim 8 wherein the patterns are etched in the bottom electrode.

16. The water quality analysis system of claim 8 wherein the fluid concentrates in a center pattern.

* * * * *

UNITED STATES PATENT AND TRADEMARK OFFICE
CERTIFICATE OF CORRECTION

PATENT NO. : 8,198,075 B2
APPLICATION NO. : 11/271643
DATED : June 12, 2012
INVENTOR(S) : Elias Greenbaum et al.

Page 1 of 1

It is certified that error appears in the above-identified patent and that said Letters Patent is hereby corrected as shown below:

<u>On the Title Page</u>

Left column, item (73), after "TN (US)" insert --and University of Tennessee Research Foundation, Knoxville, TN (US)--.

Signed and Sealed this
Fifth Day of March, 2013

Teresa Stanek Rea
*Acting Director of the United States Patent and Trademark Office*